US005302322A

United States Patent [19]

Birtwistle

[11] Patent Number: 5,302,322
[45] Date of Patent: Apr. 12, 1994

[54] HAIR CARE COMPOSITION

[75] Inventor: David H. Birtwistle, Irby, United Kingdom

[73] Assignee: Chesebrough-Pond's USA Co., Division of Conopco, Inc., Greenwich, Conn.

[21] Appl. No.: 924,263

[22] Filed: Aug. 3, 1992

[30] Foreign Application Priority Data

Aug. 5, 1991 [GB] United Kingdom ............... 9116871

[51] Int. Cl.$^5$ .......................... C11D 3/26; C11D 1/90
[52] U.S. Cl. ............................ 252/547; 252/174.15; 252/174.17; 252/DIG. 5; 252/DIG. 13; 424/76; 424/71
[58] Field of Search ............... 424/70, 71; 252/174.15, 252/174.17, 547, DIG. 5, DIG. 13

[56] References Cited

U.S. PATENT DOCUMENTS

| 4,298,494 | 11/1980 | Parslow et al. | 252/174.16 |
|---|---|---|---|
| 4,312,813 | 1/1982 | Lindemann | 260/404.5 |
| 4,349,532 | 9/1982 | Vanlerberghe et al. | 424/47 |
| 4,654,161 | 5/1987 | Kollmeir et al. | 252/174.15 |
| 4,788,006 | 11/1988 | Bolich, Jr. et al. | 252/550 |
| 4,833,225 | 5/1989 | Schaefer | 528/28 |
| 4,891,166 | 1/1990 | Schaefer et al. | 260/404.5 |
| 5,047,177 | 9/1991 | Varco | 252/548 |
| 5,078,991 | 1/1992 | Beitwistle | 424/70 |
| 5,085,857 | 2/1992 | Reid | 424/70 |
| 5,135,742 | 8/1992 | Halloran | 424/70 |

FOREIGN PATENT DOCUMENTS

| 0017121 | 10/1980 | European Pat. Off. |
| 0240350 | 10/1987 | European Pat. Off. |
| 0400976 | 12/1990 | European Pat. Off. |
| 0432951 | 6/1991 | European Pat. Off. |
| 3719086 | 10/1988 | Fed. Rep. of Germany |
| 2144329 | 3/1985 | United Kingdom |
| 2157168 | 10/1985 | United Kingdom |
| 2161172 | 1/1986 | United Kingdom |

Primary Examiner—Linda Skaling
Assistant Examiner—Kery A. Fries
Attorney, Agent, or Firm—Milton L. Honig

[57] ABSTRACT

A hair care composition suitable for use as a shampoo comprises;
(a) at least one surfactant;
(b) at least one water-insoluble end-functionalized quaternary silicone polymer capable of dissolving in said at least one surfactant; and
(c) a cationic deposition polymer.

10 Claims, No Drawings

HAIR CARE COMPOSITION

FIELD OF THE INVENTION

The present invention relates to hair care compositions and in particular to clear or opaque hair care compositions containing quaternary silicones.

BACKGROUND OF THE INVENTION

Conventional silicone-containing hair care compositions, e.g. conditioning shampoos, frequently give rise to static build-up on hair which results in the problem known as 'fly-away'; that is, hair which looks fluffy and resists combing control.

Typically, such silicone-containing hair care compositions of the prior art are opaque systems and it is known that such silicone-containing opaque systems give rise to flyaway or loss of combing control of hair. GB-A-2161172 for example describes a shampoo system comprising a quaternised polymer and organofunctional silicone. However the silicones disclosed for use in that system are water-soluble "comb" polymers and give rise to hair care compositions which are opaque or cloudy in appearance. A "comb" polymer, for the purposes of the description, is a long chain silicone polymer wherein functional groups are found scattered at various points, often randomly, along the length of the chain. Furthermore, such water-soluble silicone comb polymers have limited conditioning and non-flyaway efficacy, since their water-solubility leads to poor deposition from aqueous based shampoo compositions.

Similar disadvantages are encountered with other water-soluble silicone comb polymers also known in the art, for example the quaternary silicone polymers that are disclosed in GB-A-2157168 and GB-A-2144329.

SUMMARY OF THE INVENTION

What has now been surprisingly found is that by utilising certain water-insoluble quaternary silicones capable of dissolving in surfactant, particularly anionic surfactant, the problems associated with the prior art may be reduced. In particular, by utilising water-insoluble quaternary silicones which are not comb polymers as defined above, improved conditioning and non-flyaway benefits may be obtained over the prior art and it is possible to prepare particularly effective hair conditioning shampoo compositions which are optically clear.

According to the present invention there is provided a hair care composition suitable for use as a shampoo, comprising:
  (a) at least one surfactant;
  (b) at least one water-insoluble end-functionalised quaternary silicone polymer capable of dissolving in said at least one surfactant; and
  (c) a cationic deposition polymer.

DETAILED DESCRIPTION OF THE INVENTION (a) Surfactant

The hair care composition of the invention comprises at least one surfactant which may be selected from anionic, nonionic, amphoteric and zwitterionic surfactants or mixtures thereof.

Suitable anionic surfactants include the alkyl sulphates, alkyl ether sulphates, alkaryl sulphonates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

The nonionic surfactants suitable for use in the composition of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other suitable nonionics include mono- or di-alkyl alkanolamides. Examples include coco mono- or di-ethanolamide and coco mono-isopropanolamide.

The amphoteric surfactants suitable for se in the composition of the invention may include alkyl amine oxides, alkyl betaines, alkyl amidopropyl betaines, alkyl sulphobetaines, alkyl glycinates, alkyl carboxglycinates, alkyl amphopropionates, alkyl amidopropyl hydroxysultaines, acyl taurates and acyl glutamates wherein alkyl and acyl groups have from 8 to 18 carbon atoms. Examples include lauryl amine oxide, cocodimethyl sulphopropyl betaine and preferably lauryl betaine, cocamidopropyl betaine and sodium cocamphopropionate.

The at least one surfactant or mixture of surfactants may be present in the hair care composition of the invention in a total amount of from about 5 to about 40% by weight, more preferably from about 5 to about 20% by weight.

(b) Water-Insoluble Quaternary Silicone Polymer

The water-insoluble quaternary silicone polymer is any polymerised quaternary silicone which is end-functionalised; that is, does not fall under the ambit of the term "comb polymer" as hereinbefore defined.

Suitably, the end groups may be quaternary nitrogen-containing organs-functional end groups, so that charge on the molecule is located at the ends thereof. A suitable type of water-insoluble quaternary silicone polymer has a high chain length, typically of the order of from about 60 to about 120 units, more preferably from about 70 to about 90 units and most preferably of the order of about 80 units.

A preferred water-insoluble end-functionalised quaternary silicone polymer for use in the invention is described by the following formula:

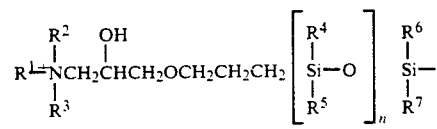

-continued

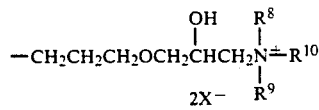

wherein $R^1$ and $R^{10}$ may be the same or different and may be independently selected from hydrogen, saturated or unsaturated long or short chain alk(en)yl, branched chain alk(en)yl, or $C_5$-$C_6$ cyclic ring systems. $R^2$, $R^3$, $R^4$, $R^5$, $R^6$, $R^7$, $R^8$ and $R^9$ may be the same or different and may be independently selected from the group consisting of hydrogen, straight chain or branched lower alk(en)yl, and $C_5$-$C_8$ cyclic ring systems. Preferably the ring systems, if any, have a sufficiently low charge such that the charge on the molecule is concentrated in the organofunctional end groups and the water insolubility of the water insoluble quaternary polymer approximates to at least that of a molecule wherein groups $R^2$-$R^9$ are methyl. Thus, the cyclic groups may be homocyclic or heterocyclic in nature, provided that the water insolubility of the molecule is at least that of a long chain molecule wherein $R^2$-$R^9$ are methyl. Thus, $R^1$, $R^2$-$R^9$ and $R^{10}$ may include nitrogen, oxygen, sulphur, carbon or phosphorus. Preferably, the ring systems comprise homocyclic rings of carbon atoms.

Alternatively, any combination of $R^1$, $R^2$ and $R^3$, and similarly any combination of $R^8$, $R^9$ and $R^{10}$, may form a ring system with the respective end nitrogen of the above formula and form such systems as morpholine or pyrrolidine.

The value of n may be of from about at least 60 or above, but must be such that the water solubility of the quaternary silicone is of the order of less than or equal to 0.001 wt. % in water at 20° C. The value of n may be an integer value lying within the range of from about 60 to about 120. Preferably n is an averaged value of the order of about 80±10, wherein such a value may not be a whole integer value, for example, n may be 80.7 or the like.

The counterion $X^-$ in the above formula is preferably acetate but may instead be for example halide, organic carboxylate, organic sulphonate or the like.

A suitable example of an end-functionalised quaternary silicone polymer according to the above formula is ABIL-QUAT 3274 (ex Goldschmidt), also identified as silicone K3474, having an n value of about 80, and wherein $R^2$ to $R^9$ are all methyl.

The end-functionalised quaternary silicone polymer may be present in the hair care composition of the present invention in an amount of from about 0.01% by weight to about 1.0% by weight, preferably in an amount of from about 0.05% to about 1.0% by weight of the total composition.

(c) Cationic Polymer

The hair care composition of the present invention also includes a cationic deposition polymer which is preferably a cationic derivative of guar gum or a cationic cellulose derivative.

Suitable cationic guar gum derivatives are those given the CTFA designation guar hydroxypropyl trimonium chloride, available commercially for example as JAGUAR C13S, which has a low degree of substitution of the cationic groups and a high viscosity. Other suitable materials include that known as JAGUAR C15, having a moderate degree of substitution and a low viscosity, JAGUAR C17 (high degree of substitution, high viscosity) and JAGUAR C16 which is a hydroxypropylated cationic guar derivative containing a low level of substituent groups as well as cationic quaternary ammonium groups. Also suitable is JAGUAR C162 which is a high transparency, medium viscosity guar derivative having a low degree of substitution.

Suitable cationic cellulose derivatives as deposition polymers include the Polymer JR series, ex Union Carbide.

The compositions of the invention may contain from about 0.01 to 1% by weight of the cationic deposition polymer, preferably from about 0.04 to about 0.5% by weight.

Other Components

The compositions of the present invention may also contain as optional components cosurfactants which act as foam modifying components. Such foam modifying components may be present in amounts up to about 10% by weight, preferably in amounts of from about 1.5% to about 3% by weight. Suitable cosurfactants include betaines such as cocoamidopropyl betaine, lauryl dimethyl betaine, cocodimethyl sulphopropyl betaine and the like. Other suitable cosurfactants include such surfactants as mono- or dialkyl alkanolamides (e.g. cocodiethanolamide), amine oxides (e.g. lauryl amine oxide), glycinates, propionates, sultaines and the like.

The hair care compositions of the invention will frequently, and advantageously, be optically clear or translucent. However, opaque or cloudy formulations in accordance with the above defined composition are still within the scope of the invention.

If desired, the compositions of the invention may also contain a suitable amount of one or more opacifiers, e.g. ethylene glycol distearate, PEG-3 distearate.

The shampoo compositions of the present invention may contain other components in minor amounts commonly found in shampoo compositions, such as antibacterial agents, antidandruff agents such as zinc pyridinethione or Octopirox, pearlescers, perfumes, dyes, colouring agents, preservatives, viscosity modifiers, proteins, polymers, buffering agents, polyols and other moisturising agents, plant extracts such as seaweed extracts, herb extracts and the like.

In a further aspect of the present invention there is provided a method of preparing the hair care composition defined above. In the method, surfactant(s) and water are mixed together, reaching homogeneity. Quaternary silicone may then be added and mixed in under high shear mixing if appropriate, until the mixture is substantially homogeneous. Cationic polymer, e.g. guar hydroxypropyl trimonium chloride, may be added either as a solid or as a solution in water. The resulting mixture may then be stirred until homogeneous. Remaining components, such as sodium chloride, perfume, colouring and like, may then be added under typical mixing conditions.

In yet a further aspect of the present invention, use of the hair care composition entails wetting the hair, then adding shampoo to the hair, typically of the order of about 5 to 10 grams of shampoo, and massaging the hair to generate a rich lather. The hair may then be rinsed until the foam is washed out. The process may be repeated.

The invention will now be illustrated by the following examples. It is to be understood that the examples are not to be viewed as limiting in any way the scope of the appended claims. All amounts are expressed in % by weight, unless otherwise stated.

EXAMPLES 1 to 21

The following hair conditioning shampoo compositions were prepared according to the method described above. The compositions of Examples 1 to 14 were optically clear, whereas those of Examples 15 to 20 were opaque.

| Example | 1 | 2 | 3 | 4 | 5 | 6 | 7 | 8 | 9 | 10 |
|---|---|---|---|---|---|---|---|---|---|---|
| SLES 2EO | 16 | 16 | 16 | 16 | 16 | 16 | — | — | — | — |
| Ammonium lauryl sulphate | — | — | — | — | — | — | 12 | 12 | 12 | 12 |
| SLES 3EO | — | — | — | — | — | — | — | — | — | — |
| Cocoamidopropyl betaine | 2 | 2 | 2 | 2 | 2 | 2 | — | — | — | — |
| Lauryl dimethyl betaine | — | — | — | — | — | — | 2 | 2 | 2 | 2 |
| Quaternary silicone* | 0.1 | 0.25 | 0.5 | 0.1 | 0.25 | 0.5 | 0.4 | 0.4 | 0.4 | 0.4 |
| Jaguar C13S | 0.1 | 0.1 | 0.1 | 0.04 | 0.04 | 0.04 | — | — | — | — |
| Jaguar C17 | — | — | — | — | — | — | 0.05 | 0.1 | 0.3 | 0.5 |
| Jaguar C162 | — | — | — | — | — | — | — | — | — | — |
| Jaguar C16 | — | — | — | — | — | — | — | — | — | — |
| Ethylene glycol distearate | — | — | — | — | — | — | — | — | — | — |
| PEG-3 distearate | — | — | — | — | — | — | — | — | — | — |
| Perfume, dyes etc | q.v. | q.v. | q.v. | q.v. | q.v. | q.v. | q.v. | q.v. | q.v. | q.v. |
| Sodium chloride | 1 | 1 | 1 | 1 | 1 | 1 | — | — | — | — |
| Ammonium chloride | — | — | — | — | — | — | 1.5 | 1.5 | 1.5 | 1.5 |
| Water | to 100 | to 100 | to 100 | to 100 | to 100 | to 100 | to 100 | to 100 | to 100 | to 100 |

| Example | 11 | 12 | 13 | 14 | 15 | 16 | 17 | 18 | 19 | 20 |
|---|---|---|---|---|---|---|---|---|---|---|
| SLES 2EO | — | — | — | — | 16 | 16 | 14 | 12 | 16 | 13 |
| Ammonium lauryl sulphate | — | — | — | — | — | — | — | — | — | — |
| SLES 3EO | 14 | 14 | 14 | 14 | — | — | — | — | — | — |
| Cocoamidopropyl betaine | — | — | — | — | 2 | 2 | 4 | 2 | 2 | 4 |
| Lauryl dimethyl betaine | 3 | 3 | 3 | 3 | — | — | — | — | — | — |
| Quaternary silicone* | 0.2 | 0.2 | 0.2 | 0.2 | 0.2 | 0.5 | 0.1 | 0.2 | 0.5 | 0.1 |
| Jaguar C13S | 0.1 | — | — | — | 0.1 | 0.1 | 0.1 | 0.1 | 0.1 | 0.1 |
| Jaguar C17 | — | 0.06 | — | — | — | — | — | — | — | — |
| Jaguar C162 | — | — | 0.5 | — | — | — | — | — | — | — |
| Jaguar C16 | — | — | — | 0.3 | — | — | — | — | — | — |
| Ethylene glycol distearate | — | — | — | — | 0.5 | 0.7 | 1.0 | — | — | — |
| PEG-3 distearate | — | — | — | — | — | — | — | 1.0 | 0.7 | 0.5 |
| Perfume, dyes etc | q.v. | q.v. | q.v. | q.v. | q.v. | q.v. | q.v. | q.v. | q.v. | q.v. |
| Sodium chloride | 1.5 | 1.5 | 1.5 | 1.5 | 1.0 | 1.0 | 1.0 | 1.5 | 1.0 | 1.0 |
| Ammonium chloride | — | — | — | — | — | — | — | — | — | — |
| Water | to 100 | to 100 | to 100 | to 100 | to 100 | to 100 | to 100 | to 100 | to 100 | to 100 |

*K3474 (ex Goldschmidt)

COMPARATIVE EXAMPLE 1

The following shampoo compositions A and B were prepared as described above. Composition A (which was optically clear) was in accordance with the invention, while Composition B included instead a water-soluble quaternary silicone polymer (ABIL-QUAT 3272, ex Goldschmidt) of a corresponding structure to silicone K3474 but in which the value of n in the formula is about 30.

| | Composition (% wt) | |
|---|---|---|
| Ingredient | A | B |
| SLES 2EO | 16 | 16 |
| Cocoamidopropyl betaine | 2 | 2 |
| Silicone K3474 | 0.5 | — |
| Silicone ABIL-QUAT 3272 | — | 0.5 |
| Jaguar C13S | 0.1 | 0.1 |
| Formalin | 0.1 | 0.1 |
| Sodium chloride | 1.0 | 1.0 |
| Water | to 100 | to 100 |

Shampoos A and B were subjected to a paired comparison test for the descriptors ease of dry combing, softness and nonflyaway, using as a control a non-conditioning shampoo formulation corresponding to A or B but excluding silicone.

The votes assigned for each of the test formulations (vs control) were as follows:

| | Votes (maximum possible 72) | |
|---|---|---|
| | A | B |
| Ease of dry combing | 70+ | 43 |
| Softness | 66+ | 28 |
| Non-flyaway | 70+ | 55 |

+ >99.99% significance.

COMPARATIVE EXAMPLE 2

The following shampoo composition C was prepared as before:

| Ingredient | C (% wt) |
|---|---|
| SLES 3EO | 8 |
| Cocoamidopropyl betaine | 4 |
| Silicone K3474 | 0.2 |
| Polymer JR400 | 0.3 |
| Formalin | 0.1 |
| Sodium chloride | 2 |
| Water | to 100 |

Shampoo C, which was transparent, was subjected to a paired comparison test for the same descriptors and versus the same control as in Comparative Example 1. The votes assigned to the test formulation (vs control) were as follows:

| | Votes (maximum possible 72) |
| --- | --- |
| | C |
| Ease of dry combing | 72⁻ |
| Softness | 66⁻ |
| Non-flyaway | 72⁻ |

⁻ >99.99% significance.

COMPARATIVE EXAMPLE 3

The following shampoo composition D in accordance with the prior art was prepared as before. The silicone used was ABIL B9950, as disclosed in GB-A-2161172, which is a watersoluble comb polymer as known from the prior art.

| Ingredient | D (% wt) |
| --- | --- |
| SLES 2EO | 16 |
| Cocoamidopropyl betaine | 2 |
| ABIL B9950 | 1 |
| Jaguar C13S | 0.1 |
| Formalin | 0.1 |
| Sodium chloride | 1.5 |
| Water | to 100 |

Shampoo D, which was transparent, was subjected to a paired comparison test for the same descriptors and versus the same control as in Comparative Example 1. The votes assigned to the test formulation (vs control) were as follows:

| | Votes (maximum possible 72) |
| --- | --- |
| | D |
| Ease of dry combing | 28 |
| Softness | 33 |
| Non-flyaway | 36 |

Each of the above results is statistically non-significant, and in all but the non-flyaway case in favour of the control.

COMPARATIVE EXAMPLE 4

The following three shampoo compositions E, F and G were prepared as before. Composition E was in accordance with the present invention, while compositions F and G included instead water-soluble quaternary silicone polymers (ABIL B9950 and ABIL B9905, respectively) as disclosed in GB-A-2161172.

| Ingredient | Composition (% wt) | | |
| --- | --- | --- | --- |
| | E | F | G |
| SLES 2EO | 16.24 | 16.24 | 16.24 |
| Coconut diethanolamide | 4.00 | 4.00 | 4.00 |
| ABIL B9950* | — | 1.00 | — |
| ABIL B9905* | — | — | 1.00 |
| K3474* | 0.30 | — | — |
| Jaguar C13S | 0.50 | 0.50 | 0.50 |
| Formalin | 0.10 | 0.10 | 0.10 |
| Water | to 100 | to 100 | to 100 |

*amounts quoted compare equivalent actual levels of silicone - ABIL B9950 and ABIL B9905 are supplied as 30% active. whereas K3474 is supplied as 100% active.

Compositions E and F were subjected to a paired comparison test between themselves for the descriptors dry combability, softness and non-flyaway. The voting split was as follows:

| | Voting split (maximum possible 72) | | |
| --- | --- | --- | --- |
| | E | vs | F |
| Dry combability | 55 | | 17 |
| Softness | 43 | | 29 |
| Non-flyaway | 49 | | 23 |

Compositions E and G were subjected to a similar but halfsize paired comparison test, between themselves, the results of which were as follows:

| | Voting split (maximum possible 36) | | |
| --- | --- | --- | --- |
| | E | vs | G |
| Dry combability | 36 | | 0 |
| Softness | —* | | —* |
| Non-flyaway | 36 | | 0 |

*for reasons of safety associated with the use of ABIL B9905, the test for softness was not able to be carried out.

We claim:

1. A hair care composition suitable for use as a shampoo, comprising:
   (a) from about 5 to about 40% by weight of at least one surfactant;
   (b) from about 0.01 to about 1.0% by weight of at least one water-insoluble end-functionalised quaternary silicone polymer represented by the following formula:

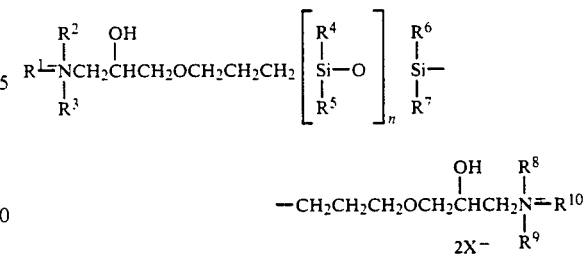

$$-CH_2CH_2CH_2OCH_2CHCH_2\overset{OH}{\underset{R^9}{\overset{|}{N}}}\overset{R^8}{\underset{}{\overset{|}{=}}}R^{10}$$
$$2X^-$$

wherein $R^1$ and $R^{10}$ are the same or different and independently selected from the group consisting of hydrogen, saturated or unsaturated long or short chain alk(en)yl, branched chain alk(en)yl, and $C_5$–$C_6$ cyclic ring systems: $R^2$, $R^3$, $R^4$, $R^5$, $R^6$, $R^7$, $R^8$ and $R^9$ are the same or different and independently selected from the group consisting of hydrogen, straight chain or branched lower alk(en)yl, and $C_5$–$C_8$ cyclic ring systems; and X— is a counterion: and wherein n has an integral or nonintegral averaged value in the range 70 to 90, said silicone polymer being capable of dissolving in said at least one surfactant; and
   (c) from about 0.01 to 1% by weight of a cationic deposition polymer.

2. A composition according to claim 1, wherein the end-functionalised quaternary silicone polymer has a water solubility of not more than 0.01 wt % in water at 20° C.

3. A composition according to claim 1, wherein the surfactant is selected from the group consisting of anionic, nonionic, amphoteric and zwitterionic surfactants and mixtures thereof.

4. A composition according to claim 1, wherein in the formula the cyclic ring system have a charge such that the water insolubility of the quaternary silicone polymer is at least that of a corresponding molecule in which the groups $R^2$ to $R^9$ are all methyl.

5. A composition according to claim 1, wherein in the formula the cyclic ring systems are selected from the group consisting of homocyclic and heterocyclic ring systems containing any atom selected from the group consisting of carbon, nitrogen, oxygen, sulphur and phosphorus.

6. A composition according to claim 1, wherein in the formula any radical combination selected from the group consisting of a combination of $R^1$, $R^2$ and $R^3$, a combination of $R^8$, $R^9$ and $R^{10}$, and mixtures thereof form a ring system with a respective end nitrogen atom.

7. A composition according to claim 1, wherein in the formula X— is selected from the group consisting of acetate, halide, organic carboxyalte and organic sulphonate.

8. A composition according to claim 1, wherein the cationic depression polymer is a cationic derivative of guar gum or a cationic cellulose derivative.

9. A composition according to claim 1, further comprising up to 10% by weight of a cosurfactant selected from the group consisting of betaines, mono- or dialkyl alkanolamides, amine oxides, amine glycinates, amine propionate and amine sultaines.

10. A method of washing hair comprising applying thereto a composition according to claim 1.

* * * * *